United States Patent [19]

Gyure et al.

[11] Patent Number: 5,584,816
[45] Date of Patent: Dec. 17, 1996

[54] HARDPACK SHIELD FOR A PIVOTING NEEDLE GUARD

[75] Inventors: Sandor Gyure, West Orange; Robert B. Odell, Franklin Lakes; Adriano Morigi, Rutherford, all of N.J.

[73] Assignee: Becton, Dickinson and Company, Franklin Lakes, N.J.

[21] Appl. No.: 450,183

[22] Filed: May 25, 1995

[51] Int. Cl.$^6$ ........................................... A61M 5/00
[52] U.S. Cl. ........................ 604/192; 604/263; 128/919
[58] Field of Search .................................. 604/110, 192, 604/187, 263; 128/919

[56] References Cited

U.S. PATENT DOCUMENTS

| | | | |
|---|---|---|---|
| D. 277,457 | 2/1985 | Lewandowski | D9/415 |
| 4,872,552 | 10/1989 | Unger | 206/365 |
| 5,055,102 | 10/1991 | Sitnik | 604/263 X |
| 5,405,332 | 4/1995 | Opalek | 604/192 |

*Primary Examiner*—John D. Yasko
*Attorney, Agent, or Firm*—Vincent A. Castiglione

[57] ABSTRACT

A hardpack shield employable with a medical delivery device utilizing the pivoting-type needle guard or barrier assembly. The shield, which may be formed from a semi-rigid yet puncture-resistant material such as polypropylene, may be configured for mating engagement with a component of the pivotable barrier assembly so as to enable a user to safely manipulate the barrier assembly respective of a medical delivery device to which the piercing element and barrier assembly are affixed. The hardpack shield is configured for ready removal by a user while providing a secondary barrier against inadvertent needlestick injury, with a piercing element.

19 Claims, 9 Drawing Sheets

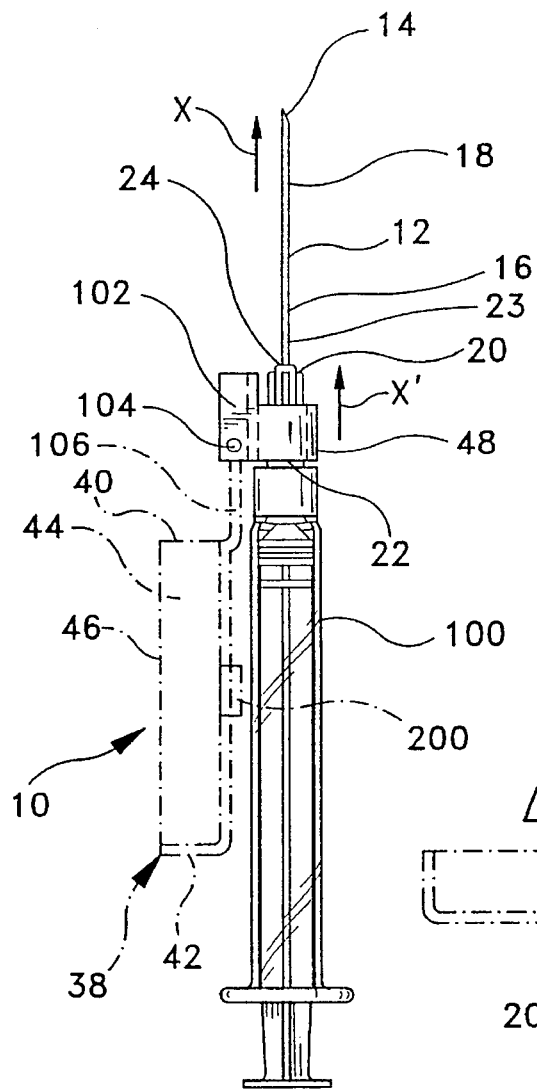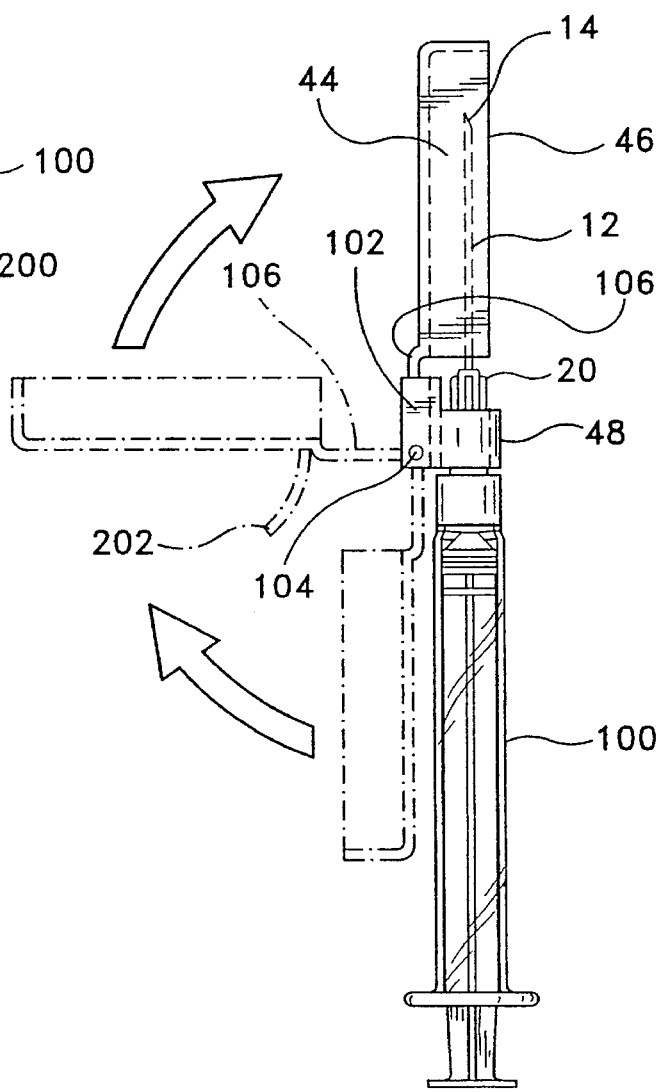

FIG-9
FIG-11
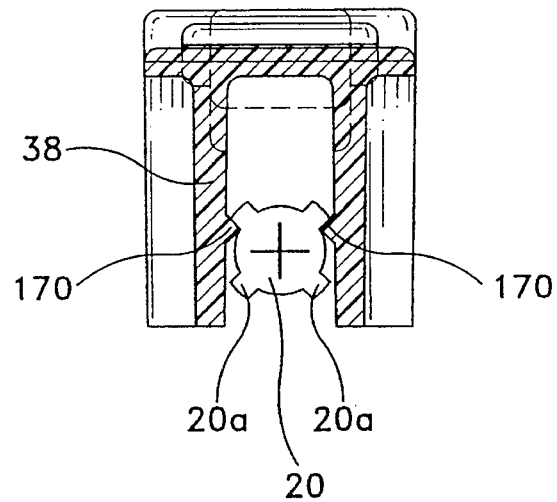
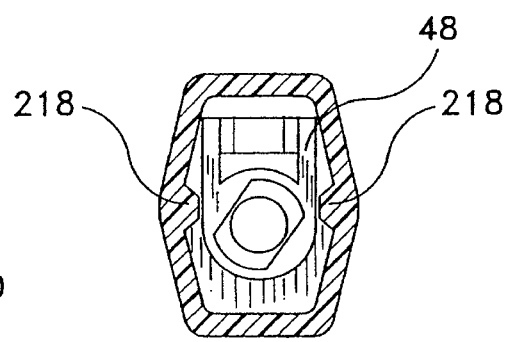
FIG-10
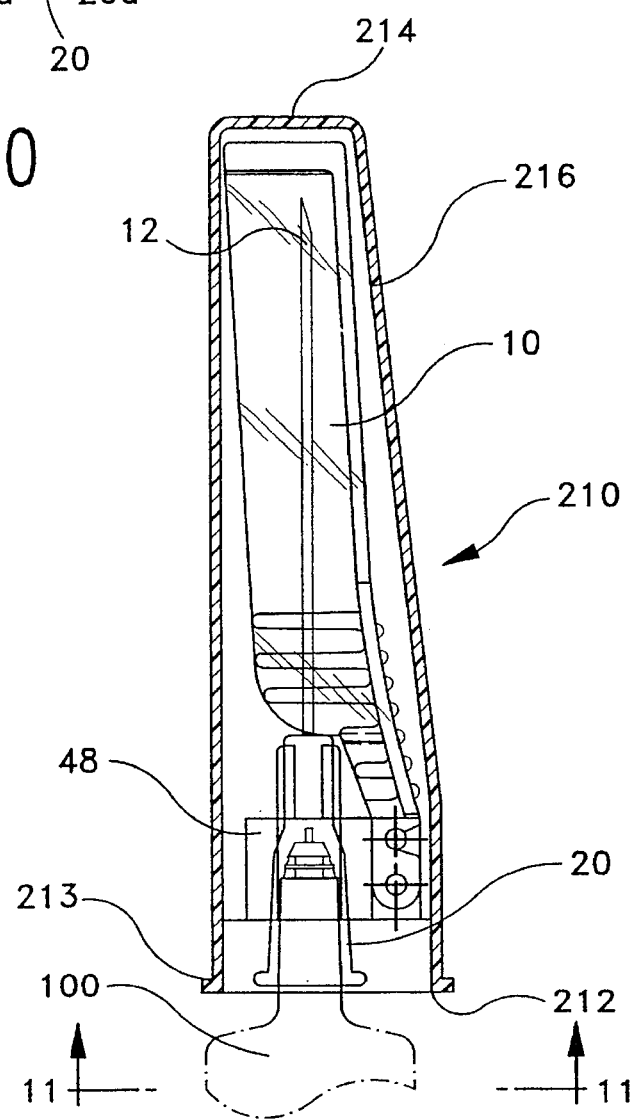

HARDPACK SHIELD FOR A PIVOTING NEEDLE GUARD

I. FIELD OF THE INVENTION

The invention relates to a shielding assembly for piercing element, and more particularly, to a removable shielding assembly for a piercing element for averting unwanted opening of a manually pivotable barrier assembly associated with said piercing element.

II. BACKGROUND

There has been a marked increase in the use of disposable medical implements, particularly medical delivery or collection implements, such as hypodermic needles/syringes or evacuated blood collection tubes Typically, such medical implements include relatively elongate piercing elements for administering a medication or withdrawing a fluid. Such piercing elements include, inter alia, pointed needle cannulae or blunt ended cannulae.

Exposure to blood borne pathogens is a recognized hazard by anyone associated with the medical arts. As a result of this recognition, numerous protocols for the use of piercing elements such as needles have been developed and are practiced. The problem of transmission of blood borne pathogens not only exists for the physician, nurse or phlebotomist using the needles, but also for support workers all through the hospital. Since most needles in use today are single-use and disposable, hospital service personnel are at risk from needles that are not properly handled by the users. A definite need has developed for ways to safely and conveniently handle and transport such implements, both during interim use of the implement and after use is completed, so that disposal can be effected while reducing the risk of exposing any person handling the used implements to injury, infection or disease by puncture or contact with a used needle.

In today's medical facilities, then, a wide variety of disposable needle devices are routinely used to administer medication by injection and intravenous ("I.V.") procedures, or for intravenous collection or withdrawal procedures such as blood collection, Either interim the completion of a procedure or once an injection is given, a blood sample drawn, or an I.V. needle removed from a patient, both the needle and/or syringe or tube used in the procedure may be contaminated and must be either handled or disposed of in a safe manner. The problem is particularly heightened because competent medical personnel will not normally leave a patient unattended immediately after administering an I.V. procedure in order to search out disposal facilities for the used medical implement. Consequently, while the nurse or physician is attending to the patient, unsheathed contaminated needles have been momentarily placed on bedside tables, the used needles have been placed on the patient's bedding, and bed mattresses have even been used as a type of "pincushion" to temporarily hold the contaminated needle.

The needle use protocols previously mentioned generally dictate in detail when and how a needle will be used and how it should be disposed of. The problem with many protocols for handling needles is that the protocols often require users to perform additional steps in a procedure With the pressure of time and simple carelessness, certain practices regarding handling of used needles are sometimes disregarded and injuries may occur.

For instance, it has been a practice to break or cut a piercing element such as a needle after use and before transport to ultimate disposal so as to eliminate the sharp end point, thereby reducing the risk of puncture, scratching or other injury which might result from handling. However, the very act of breaking or cutting the needles may expose the medical personnel to accidental puncture during the breaking or cutting operations. In addition, residual medication or blood in the needle or the syringe can splatter onto the person or his clothes, and potentially harmful fumes from the residual medication could be inhaled as a result of the so-called aerosol effect. Furthermore, the blades of the cutting tool might possibly serve as a breeding ground for germs, bacteria and other disease-causing micro-organisms to which an unsuspecting person cutting the needle could be unnecessarily exposed. Recently, an even greater danger has been recognized in connection with the handling and disposal of used needles as well as other sharp medical implements. It is now believed that certain diseases, most notably Hepatitis B, can be transmitted by covert percutaneous —i.e., by merely contacting the contaminated needle or implement.

While the used needle portion of a needle/medical implement combination presents the most significant risk of injury or injection through accidental puncture or scratching of a person's skin, the used implement part may also present a risk of infection. For example, a used implement such as a syringe, a blood collection shield, or the like can contain residual blood or medication which, if exposed to a person's skin, may be absorbed topically (particularly if a cut or break in the skin is present) and may cause a serious internal infection or other reaction. As a result of the foregoing dangers, it is preferred current practice to dispose of such devices intact, without dismantling them.

One approach for shielding a needle assembly to address the concerns voiced above might entail providing the needle assembly with a pivotable barrier assembly for protecting the elongate piercing element, inclusive of pointed needle cannulae or blunt ended needle cannulae, from inadvertent touch contact. The barrier assembly would include, for instance, a shield displaying an open end, a closed end, and an enclosing sidewall portion having a slot extending from the open end toward the closed end. In a first position, the shield is rotated away from the piercing element so that it is exposed for use. A second position is provided wherein the shield is rotated so that it substantially encloses the piercing element therein to prevent inadvertent touch contact, particularly obstructing access to the tip of the piercing element.

In this approach, numerous closing and/or locking assemblies may be provided for use of the shield. Where locking assemblies are employed, typically the shield will be securely locked in the closed position following use of the piercing element. However, in instances where it is desired to be able to reuse the piercing element, the shield may be provided with a closing assembly capable of repeated opening, allowing the shield to be releasably retained in the second position pending interim use of the implement, but structured such that the shield may be repeatedly rotatated out of the closed position. This provides a user with the ability to reuse the piercing element at will.

In either of the various locking assemblies or closing assemblies, it is typical that piercing elements will be shipped with the needle shield retained in an open position. In order to protect the piercing element from contamination during transit, a conventional cap may be placed over the piercing element so as to protect piercing element. While this is both a safe and effective approach, it would be advantageous to structure the barrier assembly with some type of a secondary sheathing element utilizable to protect the needle during shipment or prior to use, which secondary element would also provide a second degree of protection against an inadvertent touch contact with the piercing element following use, and which secondary element would also serve to permanently lock a releasable shield in place when disposal of the implement is desired..

U.S. Pat. No. 4,872,552 to Unger is directed to safety packaging for a hypodermic syringe. The device of Unger includes a pivotable shield 54 with an axially directable component 68 configured to allow a user to physically pierce the tip 16 of the needle to safeguard the user against inadvertent needlestick. An external tube-like sealing device 10 is provided for snug engagement with the cylindrical end of the syringe 18 in an effort to effect hermetic sealing of the entire structure. As depicted in the Unger reference, no contact is made between the device 10 and the other components of the device, exclusive of the syringe 18 itself.

SUMMARY OF THE INVENTION

The present invention relates to a shield for placement over a piercing element associated with a medical delivery device and utilizable prior and during use of the implement, as well as when the implement is ready for disposal. In particular, the shield may be configured for secure but releasable engagement over a pivotable barrier assembly associated with the piercing element or medical delivery device. If desired, a locking assembly may be incorporated between the shield and piercing element and/or medical delivery device to enable secure locking of the shield over the barrier assembly when disposal of the medical delivery device is desired In one embodiment, the shield may be formed with an open proximal end, a closed distal end, and a sidewall extending therebetween so as to protectively surround the entirety of the pivotable barrier assembly when the shield is placed thereover One or more ribs or other types of engaging elements may be formed in the interior of the shield to engage a component of the pivotable barrier assembly itself. A sealing element may be disposed over the open proximal end of the shield to provide a sterility maintenance seal for the barrier assembly contained in the shield during shipment. In one embodiment, the sealing element may be formed as a sealable membrane which a user can peel from the shield prior to attaching the barrier assembly to an appropriate medical delivery device. Likewise, when the barrier assembly is disposed on the medical delivery device during shipment, the shield may further be configured for added engagement with the medical delivery device in order to safeguard sterile isolation of the piercing element and/or medical delivery device. For instance, sterility seal rings may be disposed in contact with the distal end of the shield and the medical delivery device to provide a sterility maintenance seal until use is desired. If desired, the shield may be configured from a suitably puncture-resistant yet semi-rigid material such as polypropylene, polyethylene or polystyrene so that a user's squeeze action upon the shield would cause the ribs or other engaging elements to be slightly separated from their engaging contact with the barrier assembly, thus allowing the user to easily remove the shield so as to have access to the piercing element.

The shield as contemplated can serve numerous functions. It may serve as an ultimate packaging for the piercing element, preventing damage to either the barrier assembly or piercing element and maintaining their sterility; through its contact with the pivotable barrier assembly, it can serve as a means for allowing the user to attach or detach the piercing element from the medical delivery device, either during manufacture or by an end user; it can protect users from accidental touch contact with the piercing element during assembly or disassembly; it provides added protection to the piercing element from contamination with foreign matters; and it can be employed as a secondary safety cover over the pivotable barrier assembly and piercing element.

BRIEF DESCRIPTION OF THE DRAWINGS

The invention will now be described in greater detail by way of reference to the appended drawings, wherein:

FIG. 1 depicts a pivotable barrier assembly for a medical delivery device, with the barrier shown in an open position;

FIG. 2 illustrates the pivotable barrier shown in FIG. 1 in a closed position;

FIGS. 7 through 9 illustrate one way to effect a secure but releasable closing position of the pivotable barrier;

FIG. 10 depicts a protective shield utilized in accordance with the present invention in conjunction with a medical delivery device having a pivotable barrier assembly;

FIG. 11 is a cross-sectional view taken along line 11—11 of FIG. 10;

DETAILED DESCRIPTION OF THE PREFERRED EMBODIMENTS

Figure 3:
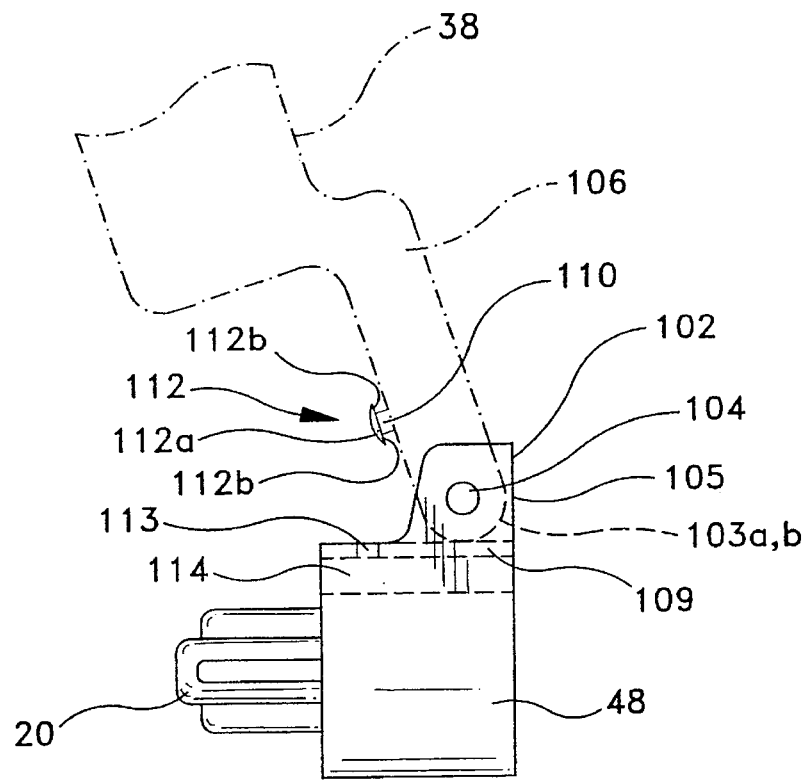
FIGS. 3 and 4 depict one way to effect locking of the pivotable barrier.

Turning now to the drawings, wherein like numerals denote like components, FIGS. 1 and 2 generally depict an assembly in accordance with the present invention utilized in conjunction with a medical delivery device such as a syringe 100. To enhance safety, the syringe 100 employs a pivotable barrier assembly 10 to protect a user from inadvertent touch contact with a piercing element 12 and, in particular, the tip 14 of the piercing element. As such, the piercing element 12 can entail such conventional fluid delivery conduits such as pointed needle cannulae made from metal, or blunt-ended cannulae formed, for instance, of various grades of medical plastics. As described herein, the term "piercing element" may be used interchangeably with the term "needle" and such recitation is intended to encompass both pointed needle cannulae as well as blunt-ended cannulae.

As illustrated, in a preferred configuration, the barrier assembly may be pivoted between an "open" position as illustrated in FIG. 1, wherein the needle 12 is exposed for use, and a "closed" position as illustrated in FIG. 27 wherein the needle 12 is protectively surrounded within the interior of a pivotable barrier 38. It will be understood and appreciated by those skilled in the art that while these embodiments of the pivotable barrier assembly of the present invention are depicted in conjunction with a syringe, they may be equally applied to other medical delivery devices such as a catheter, or to a fluid collection device such as a needle tube holder.

Figure 12:
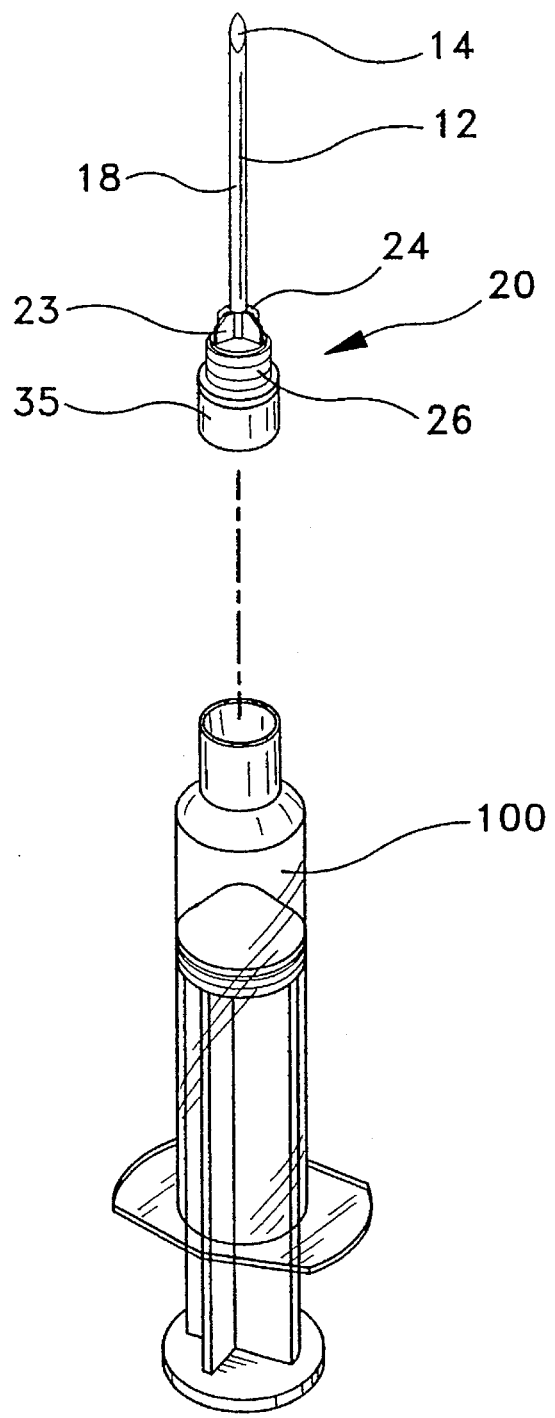
FIG. 12 is a perspective view of the piercing element mateable to a medical delivery device.

Referring to FIGS. 1, 2 and 12, the protective barrier assembly 10 of the present invention includes needle 12 having a longitudinal axis X, a pointed distal end 14, a proximal end 16 and a passageway 18 therethrough. One preferred assembly includes a hub 20 having a longitudinal axis X', a proximal end 22, a distal end 23 and an outside surface 26. Hub 20 preferably has an opening 24 for receiving needle 12 so that distal end 14 projects outwardly.

Preferably, hub 20 also includes an element 35 for releasably mounting the hub onto a fluid handling, i.e., a medical delivery, device, such as syringe 100 illustrated in the Figures. In one embodiment where the fluid handling device is a syringe 100, the elements 35 may be configured to attach the hub 20 thereon. In this embodiment, element 35 is preferably configured as a female luer lock fitting for mounting hub 20 onto a syringe 100 or other fluid handling device such as a catheter.

As previously noted, syringe 100 further employs a pivotable barrier 38, which includes a generally open end 40, a closed end 42, and a sidewall portion 44 extending, for instance, on three sides of the barrier 38. A longitudinal slot 46 is defined within the sidewall portion 44 and is formed, for instance, to accommodate needle 12 within the interior of the barrier 38. The barrier 38 is attached to the medical delivery device, for instance, by a mounting collar 48, appropriately configured and structured for attachment adjacent the distal end of the device. As seen in FIG. 1, a flange 200 may be incorporated into the structure of the barrier 38 to assist the user in operating the device. A tab element 202 (FIG. 2) may be provided, for instance, near arm 106 for the same purpose.

As herein shown, barrier 38 is hingedly affixed by an arm portion 106 via a pivot 104 mounted to a hinge portion 102 formed in mounting collar 480 While herein depicted as a pivot pin 104, it will be appreciated and understood by those skilled in the art that, if desired, arm 106 can be formed directly with hinge portion 102 and a living hinge formed in lieu of the pivot 104, It will also be appreciated and understood by those skilled in the art that hinge portion 102 and collar mounting 48 may be unitarily formed, and the sheath 38 formed unitarily with them or as a separate component. Likewise, the collar portion 48 may be formed unitarily with hub 20 or they may be formed as separate parts and then attached to one another, for instance, via adhesives welding, bonding or mechanical affixation methods within the realm of the skilled artisan. Moreover, if desired, collar mounting portion 48 and hub 20 may be configured for rotatable interaction. Also, if desired, arm portion 106 can be configured to surround hinge portion 102, the pivot pin 104 laterally passing through hinge portion 102 and through opposing, surrounding sides of arm portion 106.

As the skilled artisan will appreciate, various "locking" assemblies may be incorporated with the barrier assembly of the present invention to provide for secure locking of the barrier 38 respective of needle 12. However, to retain the ability to repeatedly maneuver barrier 38 between the open position illustrated in FIG. 1 and the closed position illustrated in FIG. 2, a closing assembly may be substituted for a locking assembly. It is within the purview of the present invention that the shield 210 may be utilized either with permanently lockable barriers or releasably closed barriers.

Figure 4:
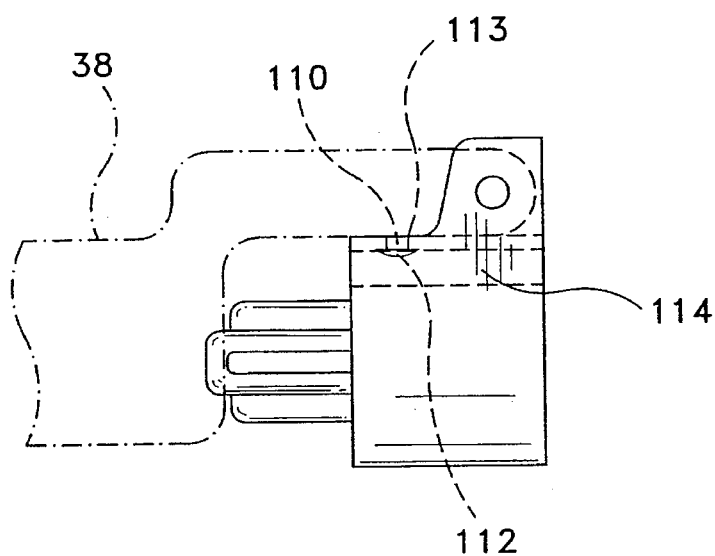

Referring to FIGS. 3 and 4, one embodiment of a locking mechanism for use with a safety needle assembly of the present invention is disclosed. Here, hinge portion 102 is affixed to the side of collar mounting 48 and is formed, for instance, as a pair of parallel sidewalls 103a, b which define a channel 105 therebetween. Arm portion 106 is pivotably mounted between sidewalls 103a, b within the channel 105 via pivot pin 104 A second channel 114 may be defined between collar mounting 48 and hinge portion 102, for instance, via a wall portion 109 dividing the hinge portion 102 from the overall collar mounting 48.

As illustrated, a hole or opening 113 may be formed through the wall portion 109, distally of the pivot point defined by pivot 104. A locking pin 110 is provided on the arm portion 106 of barrier 38, with the pin including a mushroom-shaped head 112 at the tip of pin 110. As shown, mushroom-shaped heat 112 is wider than the shaft of pin 110. While here shown that locking pin 110 is formed on the arm 106 while opening 113 is formed through wall portion 109, it will be evident to the skilled artisan that pin 110 can be provided in conjunction with channel 105 or hinge portion 102 while hole 113 can be formed on arm 106. Also, while here shown that head 112 is mushroom-shaped, it will be evident to the skilled artisan that other shapes such as barbs, arrowheads, and the like can also be employed.

As illustrated, the mushroom-shaped head 112 of the pin 110 is configured slightly wider than the hole 113 disposed through wall 109. Thus, when the shield is pivoted to the locked position illustrated in FIG. 4, the mushroom-shaped head will be compressed through the hole 113 and re-expand as it enters channel 114 The head will thus be thrust flush against the wall 109 so as to prevent the barrier 38 from being re-pivoted to re-expose the needle piercing element 12. Note that the rounded head surface 112b of the pin will be engaged against the wall portion 109 surrounding hole 113 subsequent to locking and contribute to the pin's retention with the collar mounting 48. Note also that pin 110 itself or at least its mushroom-shaped head 112 should be formed from a material which is somewhat resilient so as to be compressed through hole 113 as the lever arm 106 is rotated into locked position, but which will resist recompression through hole 113 to prevent barrier 38 from being reversed to the open position. For instance, polypropylene may be employed.

Figure 5:
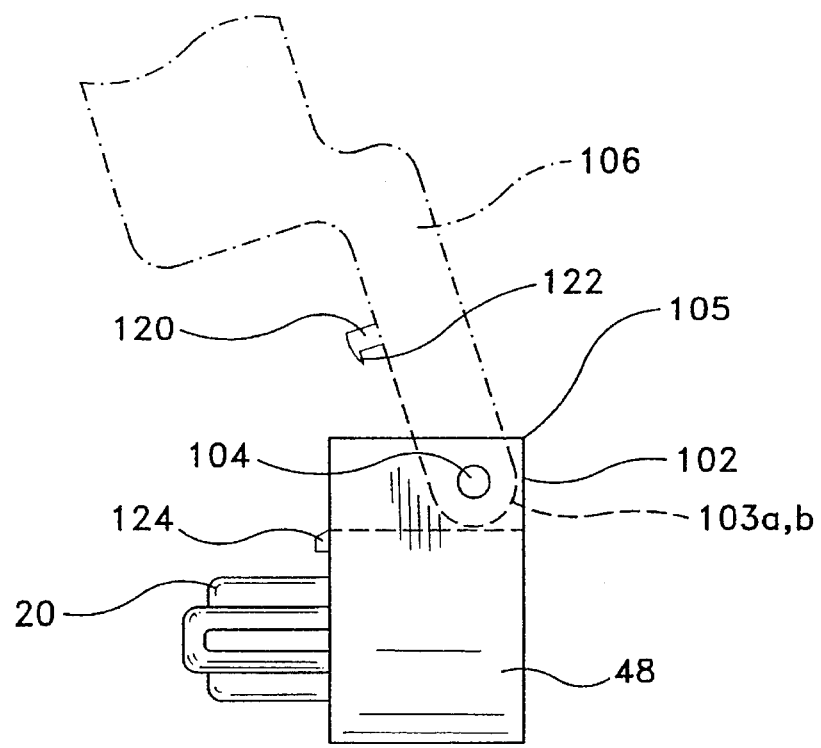
FIGS. 5 and 6 depict a second way to effect locking of the pivotable barrier.
Figure 6:
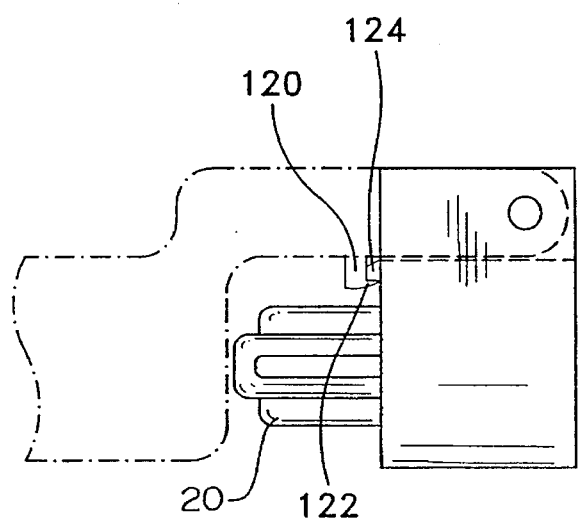

FIGS. 5 and 6 depict another embodiment of a locking mechanism for use with a safety needle assembly of the present invention. Again, arm 106 is pivotably connected to hinge portion 102 in a channel 105 formed by parallel plates 103a, b. A locking pin 120 is disposed, formed, or otherwise affixed to arm portion 106 at a point distal from pivot 104. The locking pin 120 features a hooked end 122 configured to be retained by a protrusion or detent element 124 formed on the collar mounting 48. Thus, as seen in the Figures, when barrier 38 is rotated into the locked position, hooked end 122 is urged over the detent element 124 to be retained beneath and against the protrusion 124, thereby irreversibly locking the barrier 38 in a secure position relative to needle 120

Figure 7:
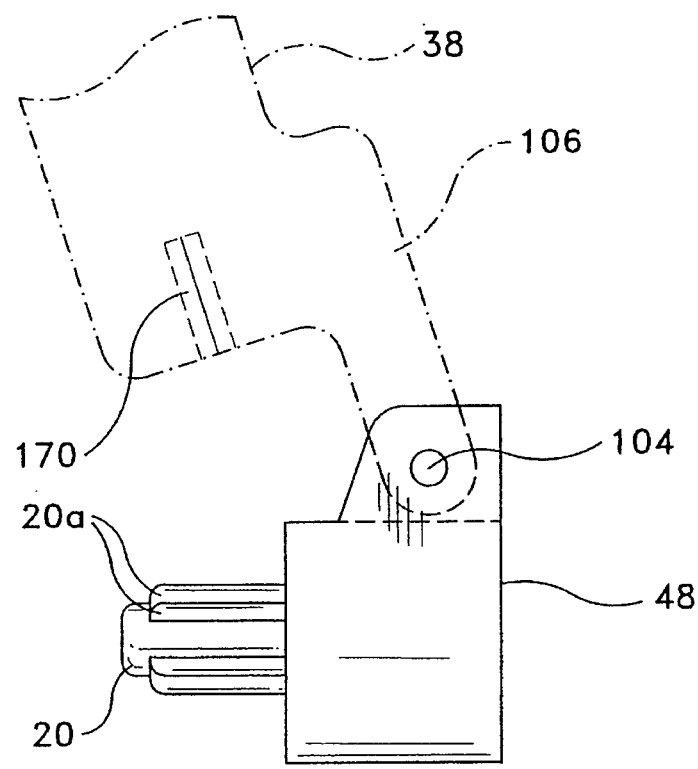
Figure 8:
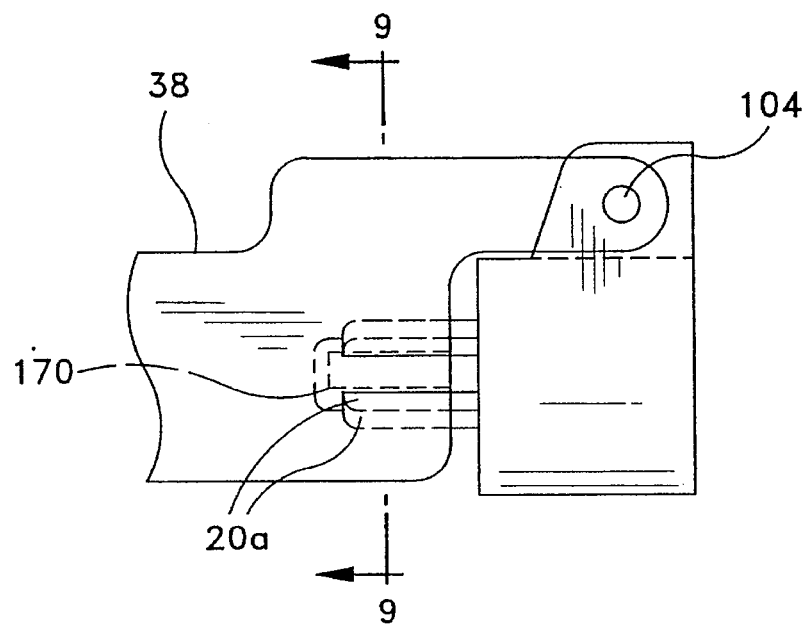

Depicted in FIGS. 7 through 9 is one embodiment of a closing assembly for use with the present invention enabling to secure repeated but releasable closure of the barrier with respect to the piercing element. A pair of rib elements 170 are formed longitudinally aligned with the barrier 38 in a manner so as to be engageable with the individual riblets 20a associated with hub 20 of the piercing element. As here depicted, the rib elements 170 are formed on an interior portion of barrier 38. When the shield is rotated into its closed position, rib elements 170 are thrust into engagement beneath riblets 20a (as best seen in FIG. 9) so as to securely keep the barrier 38 in a closed position. However, the barrier 38 is releasable by a user upon an opening force exerted upon the barrier. Note that with this embodiment, the user is given both tactile and audible indication of secure latching of barrier 38 with respect to hub 20, a useful feature when, for instance, the exigencies of the operating situation dictate rapid use of the product.

Depicted in FIGS. 10 and 11 is one embodiment of a so-called "hardpack" shield 210 utilizable with the pivotable barrier assembly as herein described, in accordance with the present invention. As shown, the hardpack shield 210 may be configured according to the dimensions and shape of a respective barrier assembly 10 utilized with the medical delivery device 100 Here, hardpack shield 210 includes a relatively open proximal end 212, a closed distal end 214, and a sidewall 216 extending therebetween. If desired, the outside surface of sidewall 216 or selected portions thereof can be provided with a textured surface to enhance a user's grip of the device. In a similar vein, ridge 213 may be formed adjacent the proximal end 212 to assist a user's manipulation.

The hardpack shield 210 further includes one or more rib elements 218 located in an interior portion of the shield 210. The rib elements 218, either formed integrally with shield 210 or formed separately and thereafter affixed to the shield, are preferably configured for mating contact with a portion of the barrier assembly 10. Conversely, it will be realized that, if desired, the ribs 218 may be formed on the collar 48 for engagement with the interior surface of shield 210. Here, rib elements 218 are configured for engagement with collar 48 of barrier assembly 10. By forming hardpack shield 210 from a puncture resistant yet resilient material such as polypropylene, the user may effectively and easily disengage hardpack shield 210 from the barrier assembly 10, for instance, by squeezing the sidewall 216 of the shield 210, causing the sidewall 216 to flex and, by consequence, urging the ribs 218 to become disengaged from collar portion 48 for ready removal. It will be understood and appreciated by the skilled artisan that in lieu of ribs, other configurations are possible. For instance, elements 218 may be formed as one or more discs or tabs, either contacting the collar 48 at its surface or mating therewith via appropriately shaped indentations formed in the collar; this construction may also be reversed, Likewise, a screw threaded arrangement may also be contemplated between shield 210 and collar portion 48, and if so configured, the handedness of the thread formed between shield 210/collar 48 versus that linking needle hub 20 with syringe 100 (such as elements 32) may be reversed, for purposes soon to be described.

Figure 14A:
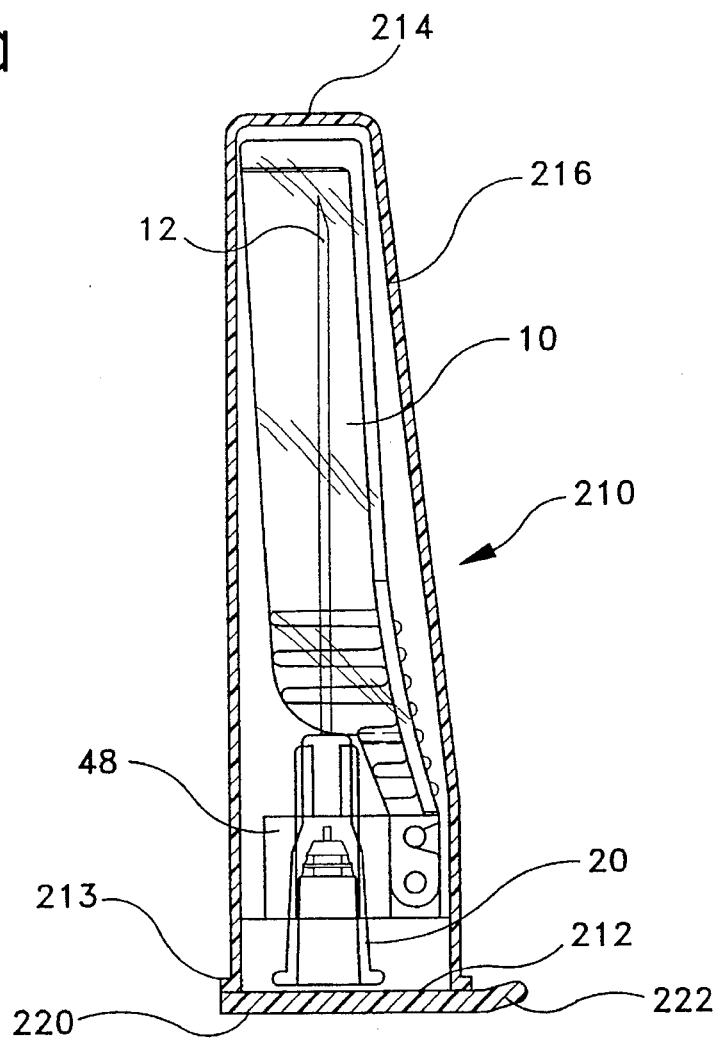
FIG. 14 (14a, 14b and 14c) depicts various sealing elements for sterility maintenance of the barrier assembly.
Figure 14B:
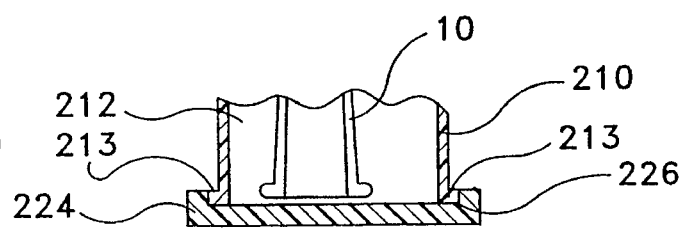
Figure 14C:
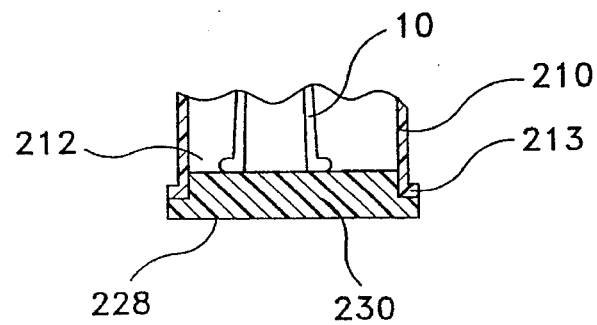

In accordance with the device, hardpack shield 210 may be shipped pre-attached to the barrier assembly 10, with rib elements 218 engaged against collar 48 of barrier assembly 10. Thus, hardpack shield 210 may serve as ultimate packaging for the entire device, eliminating the necessity for a conventional needle cap disposed about a potentially exposed piercing element 12, As depicted in FIGS. 14a to 14c, where the shield 210 is shipped already disposed about the barrier assembly 10, if desired, a sealing element may be incorporated to seal the open proximal end 212 of the shield 210 to isolate the barrier assembly 10 from contamination. The sealing element may be formed, for instance, as a peelable membrane 220 (FIG. 14a) made of an appropriate foil, plastic, or laminate, The membrane 220 may be adhesively bound to the proximal end 212, for instance, at the flange 213. A tab 222 can be provided to assist a user in removing the membrane when use is desired. Alternately, a cap 224 (FIG. 14b) formed of plastic, metal, or like material can be disposed at the proximal end 212 for snap fit, threaded engagement, or other convenient engagement with the shield 210; as here depicted, the cap 224 mates with flange 213 at an interface 226. Likewise, as seen in FIG. 14c, a plug 228 can be disposed for sealing contact with the open proximal end 212. A portion 230 of plug 228 may be disposed to jut through the open end 212 for contact with the interior of shield 210. Other sealing elements will be readily appreciated by the skilled artisan.

Advantageously, by providing ribs 218 in the interior portion of hardpack shield 210 for engagement with a portion of barrier assembly 10 such as collar 48, the device is rendered extremely versatile. For instance, a user desiring to safely remove needle 12 from the medical delivery device 100 can do so via engagement between the hardpack shield 210 and the barrier assembly 10 itself, simply by rotating the hardpack shield 210, causing hub 20 to be disengaged from medical delivery device 100. The hardpack shield 210 will remain engaged with the barrier assembly 10/needle 12, allowing both to be safely disposed of separate from the delivery device 100 if so desired, If a threaded configuration is provided in lieu of ribs, reversing the thread between shield 210/collar 48 vis-à-vis that thread linking hub 20/syringe 100 allows a user to remove the needle 12 from the syringe 100 while the shield 210 remains firmly attached to the collar 48; likewise, the shield 210 can be removed from the barrier assembly 10 without detaching needle 12 from hub 20.

Hardpack shield 210 also serves as a secondary barrier to barrier assembly 10 to safeguard a user from inadvertent needlesticks pending disposal of the device 100. In particular, after barrier 38 has been positioned in its closed state respective of piercing element 12, a user may safely re-insert hardpack shield 210 over the barrier assembly 10, both safeguarding against inadvertent re-opening of shield 38 during disposal, and to provide a secondary barrier averting needlestick injury by piercing element 12.

Figure 13A:
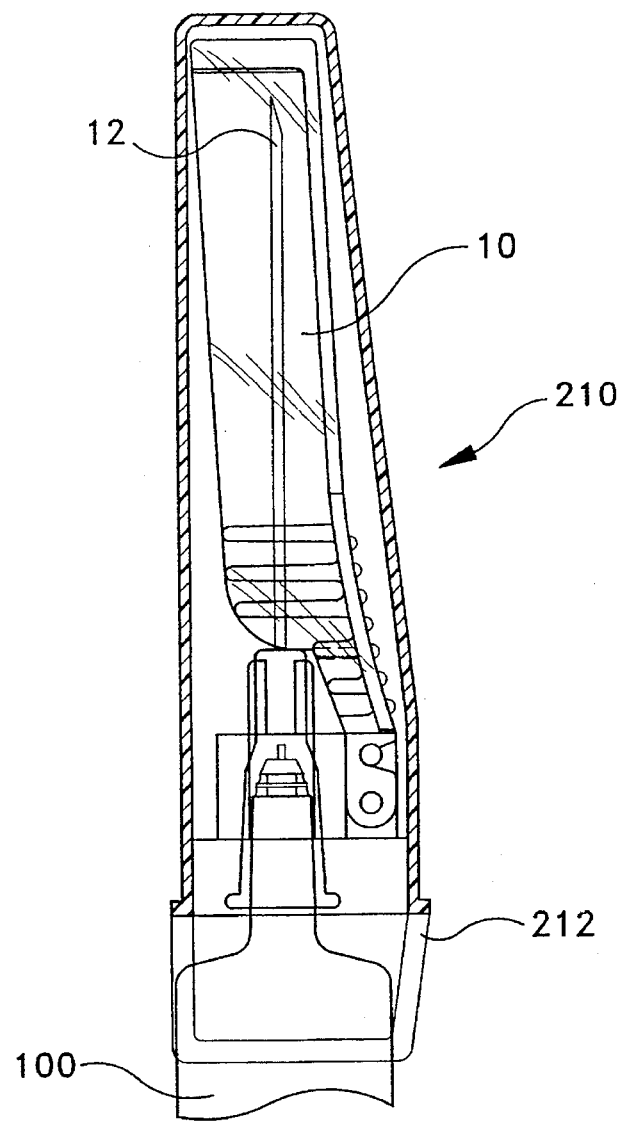
FIG. 13 (13a and 13b) depicts an alternate construction of a protective shield for the pivotable barrier assembly.
Figure 13B:
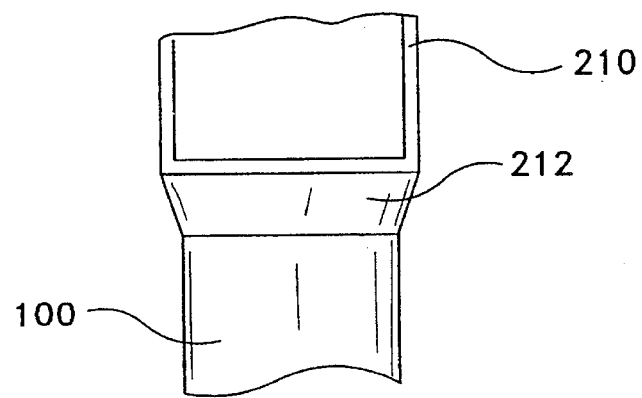
Figure 15A:
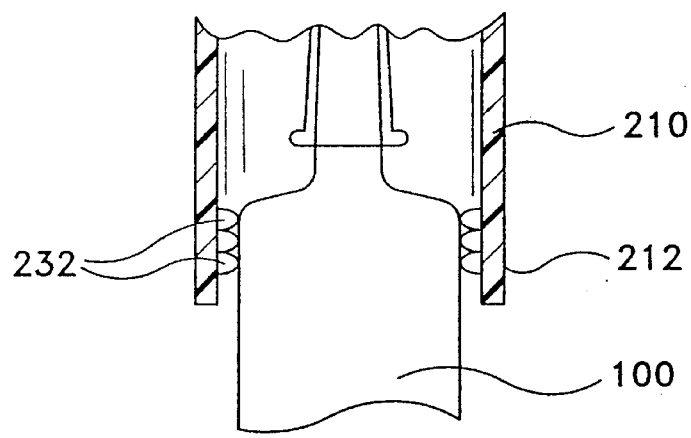
FIG. 15 (15a and 315b) depicts alternate sealing mechanisms for sterility maintenance of the barrier assembly when shipped attached to a medical delivery instrument.
Figure 15B:
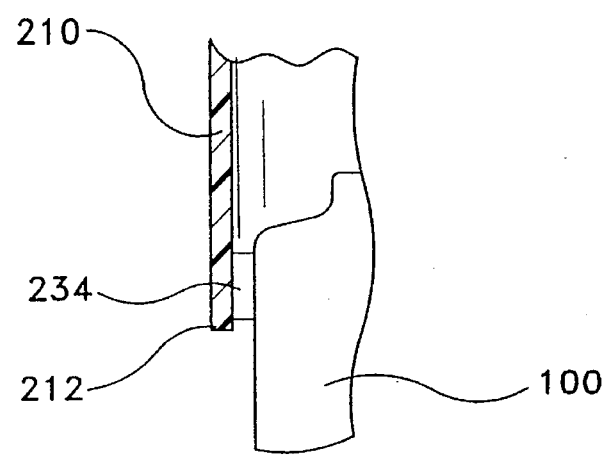

While hardpack shield 210 as set forth herein is primarily configured for engagement with a component of barrier assembly 10, it will be realized and understood by the skilled artisan that, if desired, hardpack shield 210 can be configured to enhance or otherwise preserve sterility isolation for both the needle 12/medical delivery device 100, particularly where the needle 12 is shipped pre-attached to the medical delivery device. For instance, as depicted in FIG. 3, a relatively restricted proximal end 212 may be formed in lieu of the relatively open end 212 as depicted in the prior figures. The relatively restricted proximal end 212 may be configured for snug enclosure with a portion of the medical delivery device 100, while still retaining engaging elements such as ribs 218 in contact with a portion of barrier assembly 10. For instance, the restricted proximal end 212 can be formed as an integral pan of the construction of hardpack shield 210 itself (FIG. 13a), or formed from a separate material than forms the bulk of shield 210, e.g., forming restricted end 212 as a skirted rubber shield (FIG. 13b) that can be affixed to the shield 210 or manufactured as part of the shield 210 via a co-injection process. Similarly, as illustrated in FIGS. 15a and 15b, an internal section of shield 210 at or near the restricted end 212 can be configured with sealing rings, such as a plurality of sealing rings 232 (FIG. 15a) or a single sealing ring 234 (FIG. 15b). The sealing rings, made preferably of a polymer such as polypropylene or polyethylene, can be formed separately from the shield 210 and thereafter attached or formed integrally with the shield such as through a co-injection process, and are located for sealing contact with a portion of medical delivery device 100. It will also be realized that sealing rings 232 can be formed of a silicone or rubber material. Thus, while the advantages of the hardpack shield 210 disclosed hereinabove are retained, permitting the user a variety of manipulations respective of the barrier assembly 10 and medical delivery device 100, sterility device 100 and, in particular, piercing element 12, can still be preserved before use of the device is desired.

It will appreciated and understood by the skilled artisan that further and additional forms of the present invention may be devised without departing from the spirit and scope of the appended claims, the invention not being limited to the specific embodiments shown.

We claim:

1. A protective barrier assembly for a piercing element, comprising:

a relatively elongate piercing element having a distal end and a proximal end;

a barrier element for selectively averting touch contact with said piercing element, said barrier element comprising a collar portion secured adjacent the proximal end of the piercing element and a relatively elongate channel portion pivotably secured to the collar portion, said channel portion pivotable between a first position wherein the distal end of said piercing element is uncovered and a second position wherein the distal end of the piercing element is protectively covered; and a shield defining an enclosed interior placeable over said barrier element, said shield releasably securable to a portion of said barrier assembly, said shield comprising one or more mating elements disposed in said enclosed interior, the one or more mating elements releasably securable with the collar portion of said barrier assembly.

2. The protective barrier assembly of claim 1, wherein said one or more mating elements comprise ribs disposed in said enclosed interior.

3. The protective barrier assembly of claim 1, wherein said one or more mating elements comprise a thread disposed on said enclosed interior mateable with a corresponding thread disposed on said barrier assembly.

4. The protective barrier assembly of claim 1, wherein said piercing element is affixed to a medical delivery device.

5. The protective barrier assembly of claim 4, wherein said shield further comprises a proximal end configured for mating contact with said medical delivery device.

6. The protective barrier assembly of claim 5, wherein said proximal end is formed as a separate component affixed to said shield.

7. The protective barrier assembly of claim 6, wherein said separate component comprises a rubber skin.

8. The protective barrier assembly of claim 5, wherein said proximal end comprises one or more sealing rings disposed for sealing contact with said medical delivery device.

9. The protective barrier assembly of claim 1, wherein said shield comprises a proximal end defining an opening to permit placement of the shield over the barrier assembly, wherein a removable sealing element is disposed over the opening.

10. The protective barrier assembly of claim 9, wherein the removable sealing element comprises a membrane affixed over said opening.

11. The protective barrier assembly of claim 9, wherein the removable sealing element comprises a cap disposed over said opening.

12. The protective barrier assembly of claim 9, wherein the removable sealing element comprises a plug disposed for sealing contact with said opening.

13. The protective barrier assembly of claim 1, wherein said shield is formed of polypropylene.

14. The protective barrier assembly of claim 1, wherein said shield further comprises a ridge adjacent a proximal end of the shield.

15. The protective barrier assembly of claim 1, wherein said shield includes a textured surface.

16. The protective barrier assembly of claim 1, further comprising a retaining element for retaining said channel portion in said second position.

17. A protective barrier assembly for a piercing element, comprising:

a relatively elongate piercing element having a distal end and a proximal end;

a barrier element for selectively averting touch contact with said piercing element, said barrier element comprising a collar portion secured adjacent the proximal end of the piercing element and a relatively elongate channel portion pivotably secured to the collar portion, said channel portion pivotable between a first position wherein the distal end of said piercing element is uncovered and a second position wherein the distal end of the piercing element is protectively covered; and a shield defining an enclosed interior placeable over said barrier element, said shield releasably securable to a portion of said barrier assembly, wherein said shield comprises a closed distal end;

a proximal end defining an opening to permit placement of the shield over said barrier assembly;

a sidewall extending between said distal and proximal ends to define said enclosed interior; and one or more ribs formed in said closed interior adjacent said proximal end for releasable but secure engagement with the collar portion of said barrier assembly.

18. The protective barrier assembly of claim 17, further comprising a removable sealing element disposed over said opening.

19. The protective barrier assembly of claim 17, wherein said proximal end is configured for sealing contact with a medical delivery device.

* * * * *